United States Patent
Wixey et al.

(10) Patent No.: US 7,681,575 B2
(45) Date of Patent: *Mar. 23, 2010

(54) BREATHING ASSISTANCE APPARATUS

(75) Inventors: David Fraser Wixey, Auckland (NZ); Alastair Edwin McAuley, Auckland (NZ); Christopher Earl Nightingale, London (GB); Lewis George Gradon, Auckland (NZ); Ivan Milivojevic, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 11/936,504

(22) Filed: Nov. 7, 2007

(65) Prior Publication Data

US 2008/0060650 A1    Mar. 13, 2008

Related U.S. Application Data

(63) Continuation of application No. 10/518,331, filed as application No. PCT/NZ03/00152 on Jul. 11, 2003, now Pat. No. 7,308,895.

(30) Foreign Application Priority Data

Jul. 12, 2002    (NZ) .................................. 520167

(51) Int. Cl.
*A61M 16/00*    (2006.01)
(52) U.S. Cl. ..................... 128/206.21; 128/207.13; 128/206.24
(58) Field of Classification Search ............ 128/206.12, 128/206.18, 206.21, 206.22, 206.24, 206.28, 128/207.12, 207.13
See application file for complete search history.

(56) References Cited

U.S. PATENT DOCUMENTS

| 5,243,971 | A | 9/1993 | Sullivan et al. |
|---|---|---|---|
| 5,570,689 | A | 11/1996 | Starr et al. |
| 6,112,746 | A | 9/2000 | Kwok et al. |
| 6,357,441 | B1 | 3/2002 | Kwok et al. |
| 6,467,482 | B1 | 10/2002 | Boussignac |
| 6,651,663 | B2 | 11/2003 | Barnett et al. |
| 6,871,649 | B2 | 3/2005 | Kwok et al. |
| 7,007,696 | B2 | 3/2006 | Palkon et al. |
| 7,107,989 | B2 | 9/2006 | Frater et al. |
| 2001/0020474 | A1 | 9/2001 | Hecker et al. |
| 2002/0100479 | A1 | 8/2002 | Scarberry et al. |
| 2003/0019495 | A1 | 1/2003 | Palkon et al. |
| 2004/0118406 | A1 | 6/2004 | Lithgow et al. |

FOREIGN PATENT DOCUMENTS

| EP | 1 258 266 | 11/2002 |
|---|---|---|
| WO | 00/53265 | 9/2000 |
| WO | 00/78384 | 12/2000 |

*Primary Examiner*—Steven O Douglas
(74) *Attorney, Agent, or Firm*—Trexler, Bushnell, Giangiorgi, Blackstone & Marr, Ltd.

(57) ABSTRACT

A patient interface is described which is reduces the pressure of the mask on the users face. The patient interface has a sealing interface having an inner sealing member and an outer sealing member. The inner and outer sealing members are adapted to seal around the facial contours of a user providing a sealed fluid communication to the user's respiratory tract. The inner and outer sealing members are at least continuously in contact with each other around the portions where the sealing interface contacts the users facial contours. The inner sealing member may be provided with cut outs to provide additional flexibility to particular areas, such as the nasal bridge, upper lip or cheek regions and may be provided with a contoured edge to better fit the facial contours of a user.

10 Claims, 13 Drawing Sheets

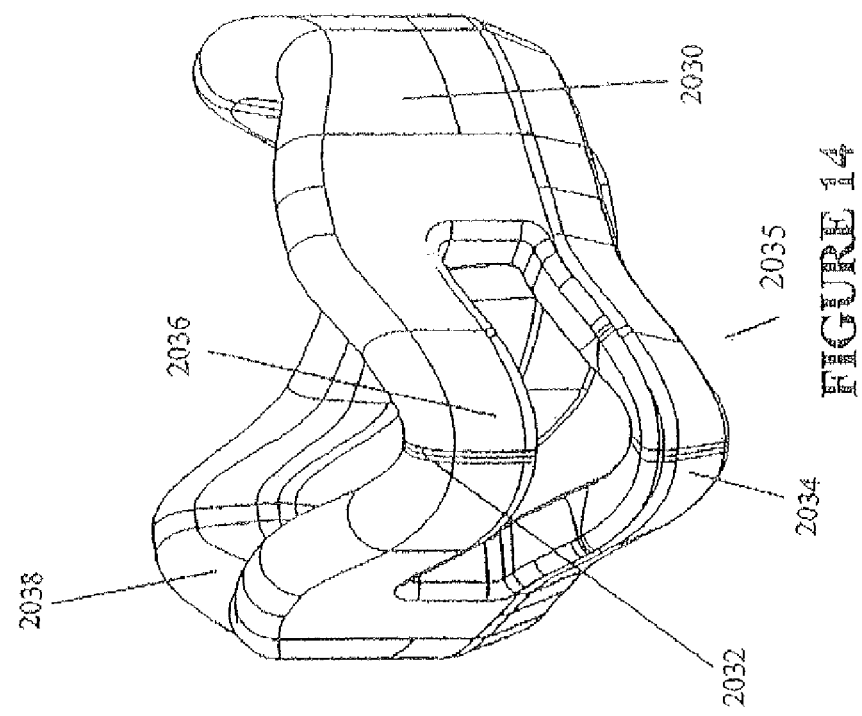
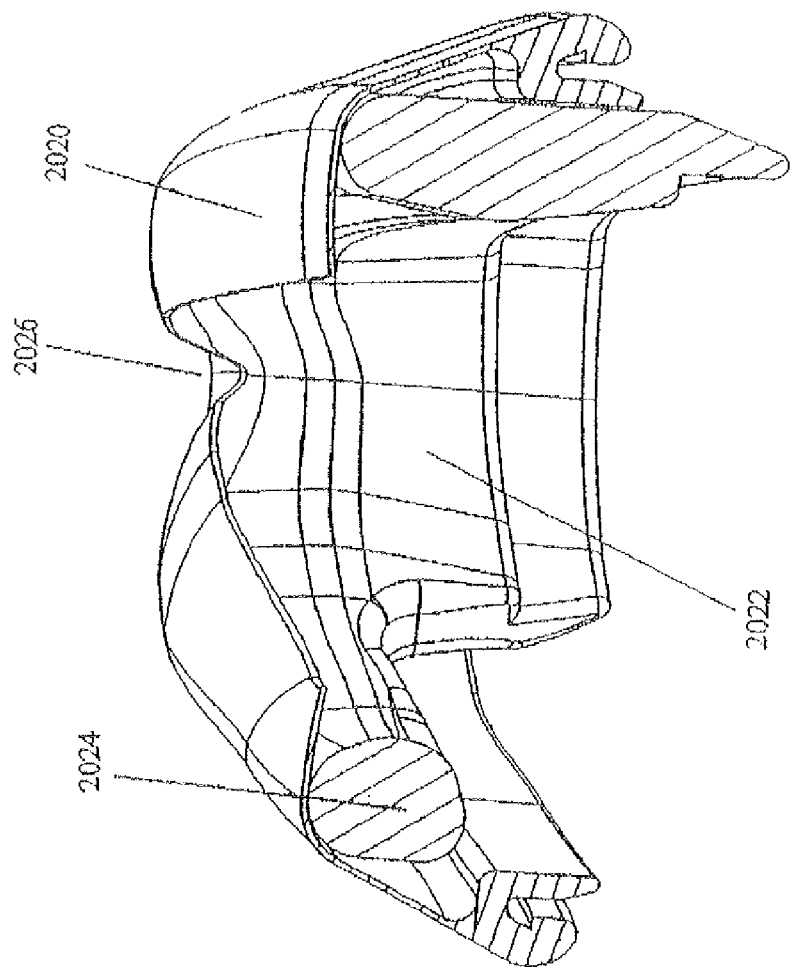

BREATHING ASSISTANCE APPARATUS

This application is a continuation of U.S. patent application Ser. No. 10/518,331 which received a 371 filing date of Jun. 27, 2005, which in turn, is the National Phase filing of PCT/NZ2003/000152, having an International filing date of Jul. 11, 2003. The disclosures of the afore-mentioned applications/patents are herein incorporated by reference.

TECHNICAL FIELD

This invention relates to patient interfaces particularly though not solely for use in delivering CPAP therapy to patients suffering from obstructive sleep apnea (OSA).

BACKGROUND ART

In the art of respiration devices, there are well known variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. No. 5,243,971 and U.S. Pat. No. 6,112,746 are examples of prior art attempts to improve the mask system U.S. Pat. No. 5,570,689 and PCT publication No. WO 00/78384 are examples of attempts to improve the forehead rest.

Where such masks are used in respiratory therapy, in particular treatment of obstructive sleep apnea (OSA) using continuance positive airway pressure (CPAP) therapy, there is generally provided in the art a vent for washout of the bias flow or expired gases to the atmosphere. Such a vent nay be provided for example, as part of the mask, or in the case of some respirators where a further conduit carries the expiratory gases, at the respirator. A further requisite of such masks is the washout of gas from the mask to ensure that carbon dioxide build up does not occur over the range of flow rates. In the typical flow rates in CPAP treatment, usually between 4 cm $H_2O$ to 20 cm $H_2O$, prior art attempts at such vents have resulted in excessive noise causing irritation to the user and any bed partners.

In common with all attempts to improve the fit, sealing and user comfort is the need to avoid a concentrated flow of air at any portion of the respiratory tracts. In particular with oral masks or mouthpieces it is a disadvantage of prior art devices that the oral cavity may become overly dehydrated by use of the device, causing irritation and possible later complications.

DISCLOSURE OF THE INVENTION

It is an object of the present invention to attempt to provide a patient interface which goes some way to overcoming the abovementioned disadvantages in the prior art or which will at least provide the industry with a useful choice.

Accordingly in a first aspect the present invention consists in a sealing interface for use with delivery of respiratory ceases to a user comprising:

an inner sealing member and an outer sealing member, each having nasal bridge, cheek and upper lip regions that are in use aligned to the nasal bridge, cheek and upper lip regions when in use on the face of said user, said inner sealing member having a cut out in the nasal bridge region, said inner sealing member and said outer sealing member adapted to seal around the facial contours of said user providing a substantially sealed fluid communication to the respiratory tract of said user.

Preferably in use said sealing interface is attached to a body that receives said gases, said sealing interface having a first bridging section and said cut out provides a gap between said body and said inner sealing member such that said first bridging section can flex within said gap.

Alternatively in use said sealing interface is attached to a body that receives said gases and said cut out is in said inner sealing member on the side of said inner sealing member abutting said body.

Alternatively in use said sealing interface is attached to a body that receives said gases and said cut out is in said inner sealing, member on the side of said inner sealing member distal said body.

Preferably said inner sealing member has a cut out region in said cheek region.

Preferably said cut out in said cheek region is on the side of said inner sealing member that abuts said outer sealing member in use.

Preferably said inner sealing member has a cut out region in said upper lip region.

Preferably said cut out in said upper lip region is on the side of said inner sealing member that abuts said outer sealing member in use.

Preferably said inner sealing member includes a second bridging section, said cut out region disposed between said first bridging section and said second bridging section.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention consists in the foregoing and also envisages constructions of which the following gives examples.

BRIEF DESCRIPTION OF THE DRAWINGS

One preferred form of the present invention will now be described with reference to the accompanying drawings in which;

FIG. 13 shows a cross section of a fourth preferred embodiment of the sealing interface of the present invention, FIG. 14 shows a perspective view of the inner sealing (foam) member according to a fifth preferred embodiment of the sealing interface of the present invention.

BEST MODES FOR CARRYING OUT THE INVENTION

The sealing interface of the present invention provides improvements in the delivery of CPAP therapy. In particular a patient interface is described which reduces the pressure of the mask on the users face and may be quieter for the user to wear and reduces the side leakage as compared with the prior art. It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to, nasal masks, oral masks and mouthpieces.

Figure 1:
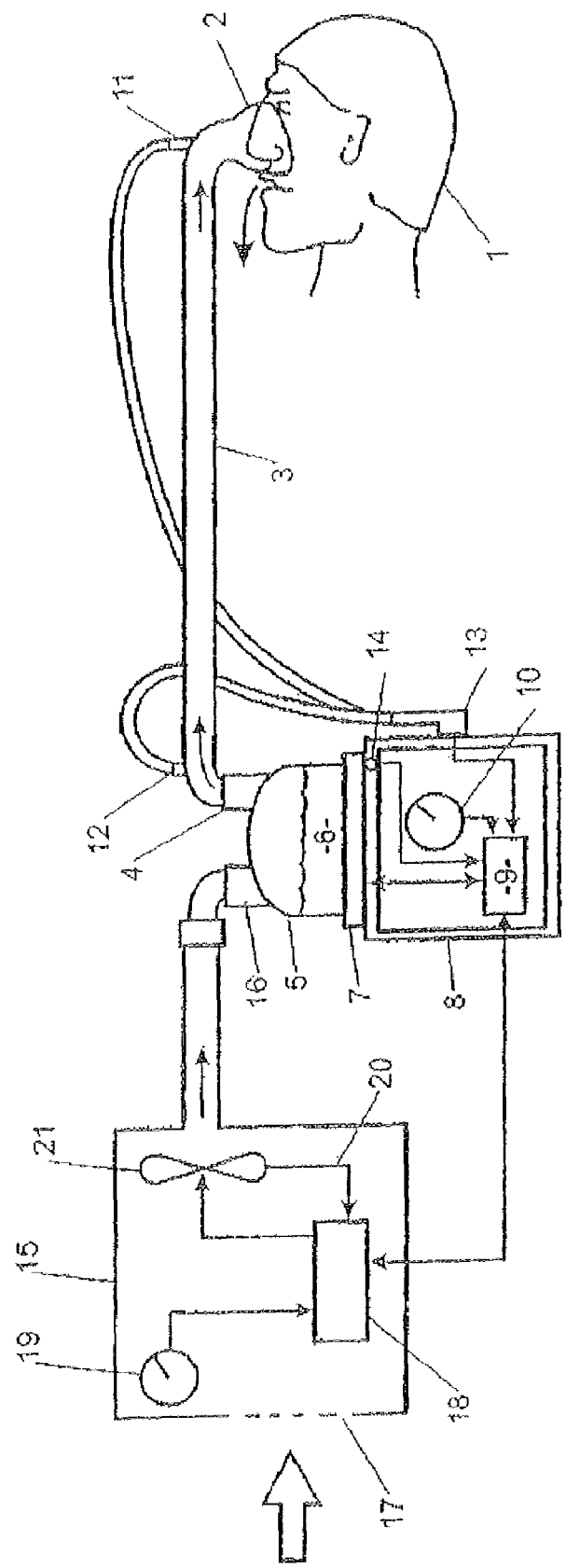
FIG. 1 is a block diagram of a humidified continuous positive airway pressure (system) as might be used in conjunction with the sealing interface of the present invention.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 5 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the low of gases (for example air) provided from a gases supply means or blower 15 which enters the chamber through inlet 16. Exhaled gases from the patient's mouth are passed directly to ambient surroundings in FIG. 1.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 2:
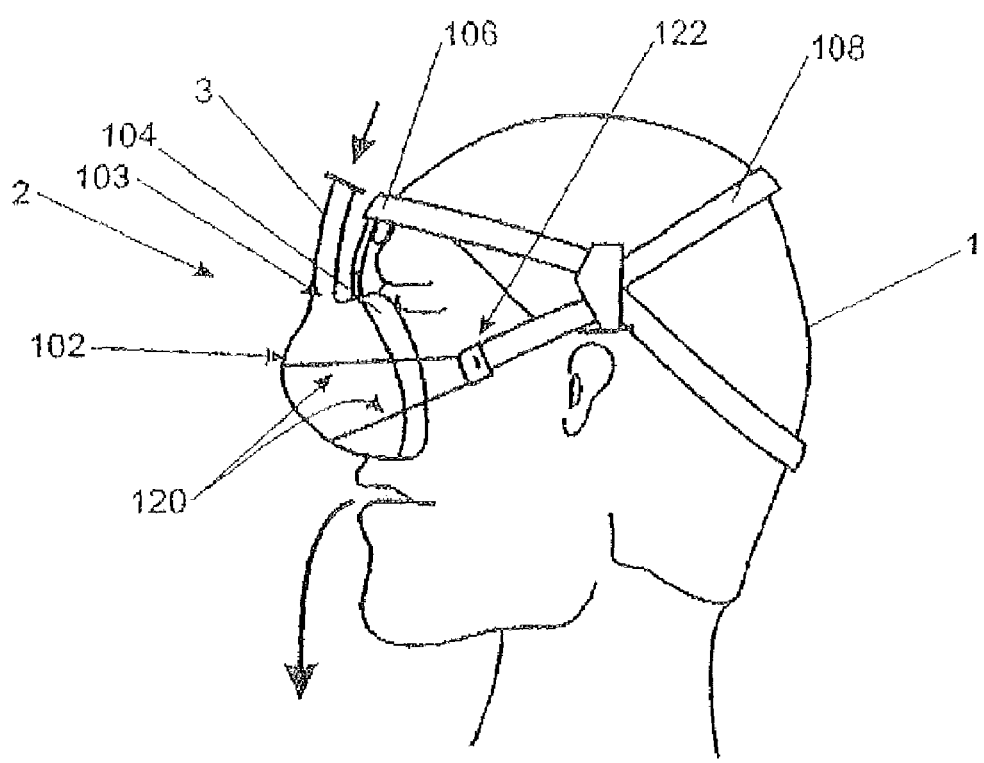
FIG. 2 is an illustration of the nasal mask including, a sealing interface in use according to the preferred embodiment of the present invention.

According to a first embodiment of the present invention the patient interface is shown in FIG. 2 as a nasal mask. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material should provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 3:
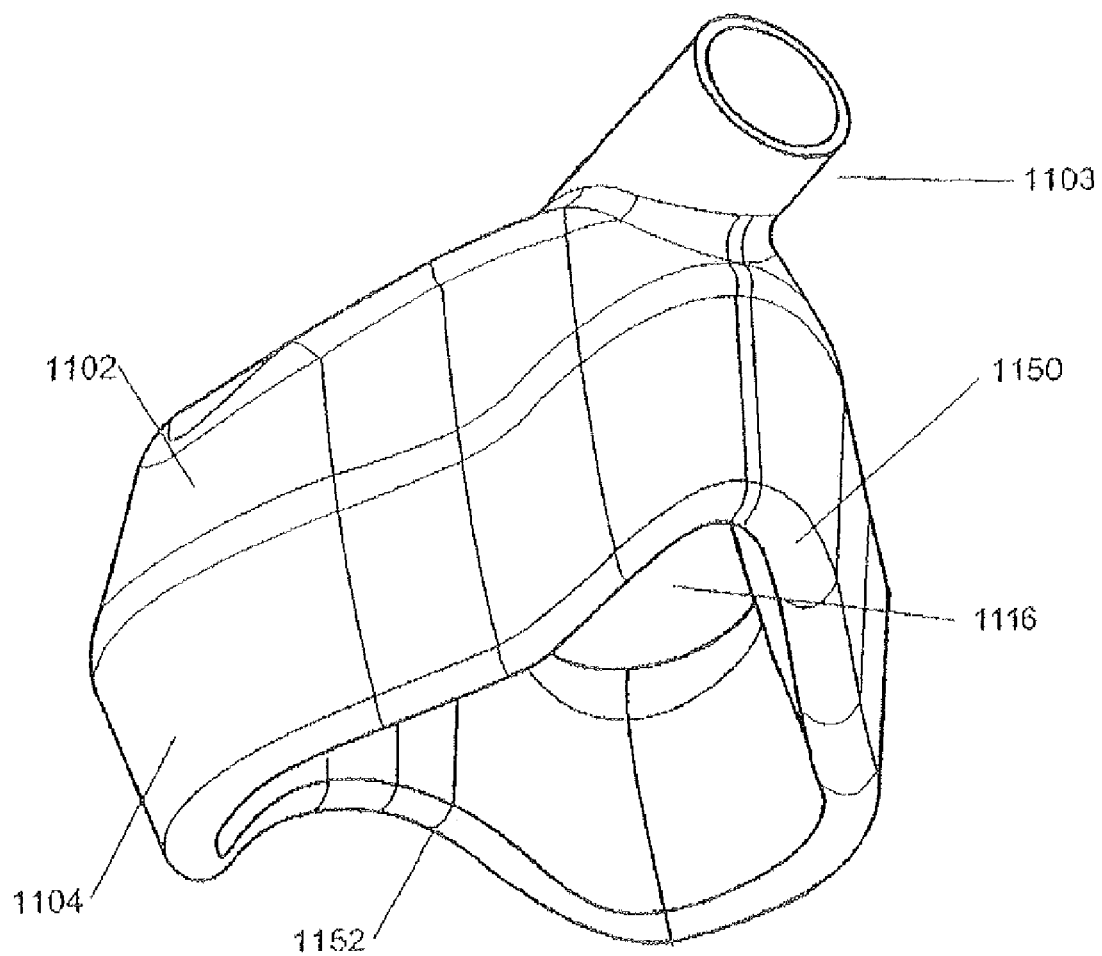
FIG. 3 shows a perspective view of a mask with a sealing interface that is a cushion.
Figure 4:
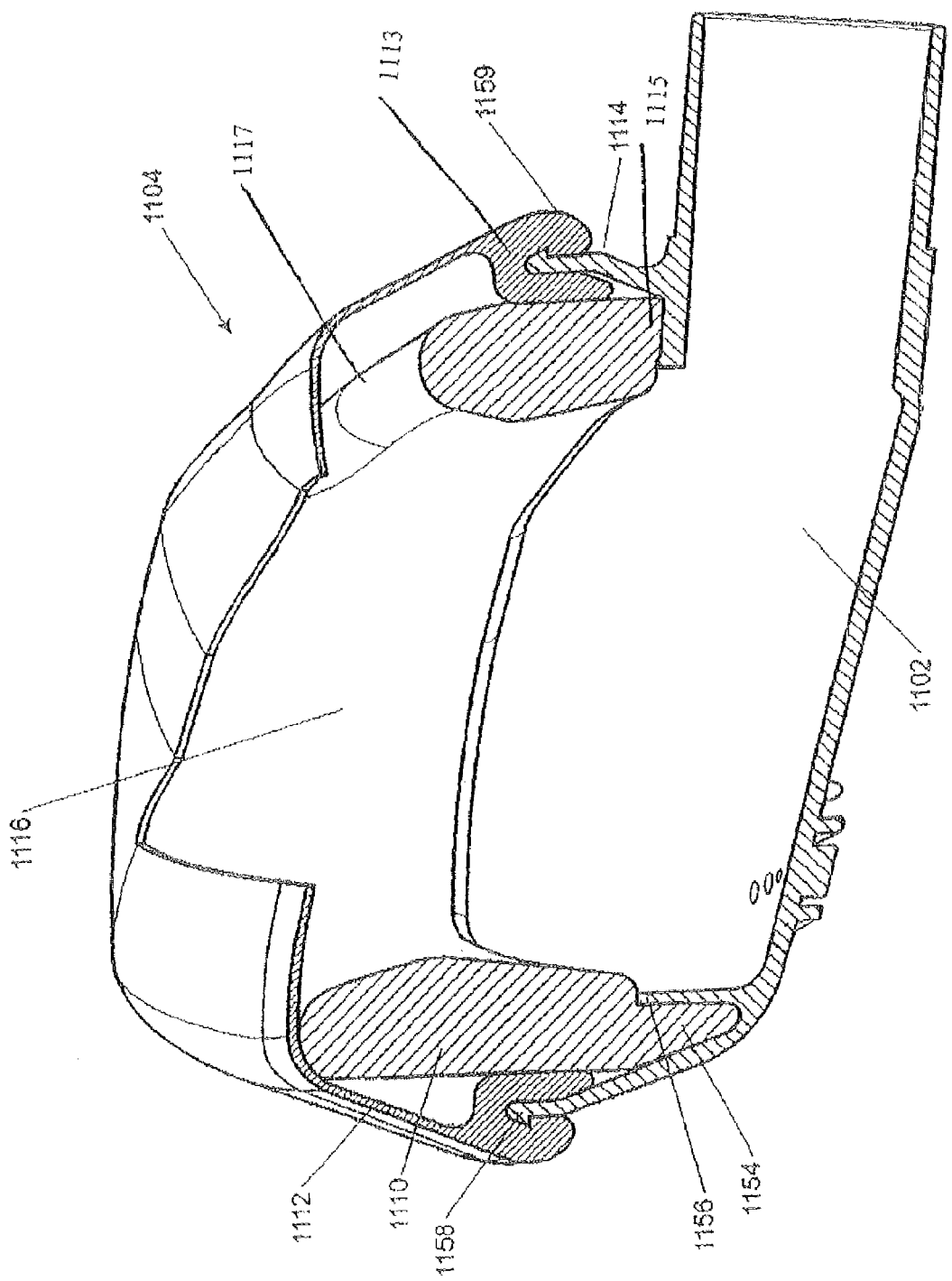
FIG. 4 is a cutaway view of the mask showing the inner sealing member and outer sealing member of the sealing interface.

Referring now to FIGS. 3 and 4 in particular, the mask cushion 1104 is provided around the periphery of the nasal mask 1102 to provide an effective seal onto the face of the user to prevent leakage. The mask cushion 1104 is shaped to approximately follow the contours of a patient's face. The mask cushion 1104 will deform when pressure is applied by the headgear 2108 (see FIG. 7) to adapt to the individual contours of any particular user. In particular, there is an indented section 1150 intended to fit over the bridge of the user's nose as well as an indented section 1152 to seal around the section beneath the nose and above the upper lip.

In FIG. 4 we see that the mask cushion 1104 is composed of an inner foam cushion 1110 covered by an outer sealing sheath 1112. The inner cushion 1110 is constructed of a resilient material for example polyurethane foam, to distribute the pressure evenly along the seal around the user's face. The inner cushion 1110 is located around the outer periphery 1114 of the open face 1116 off the hollow body 1102. Similarly the outer sheath 1112 may be commonly attached at its base 1113 to the periphery 1114 and loosely covers over the top of the inner cushion 1110.

Figure 5:
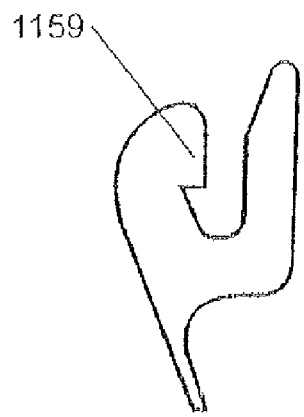
FIG. 5 is a cutaway view of the periphery of the outer sealing member or membrane.
Figure 6:
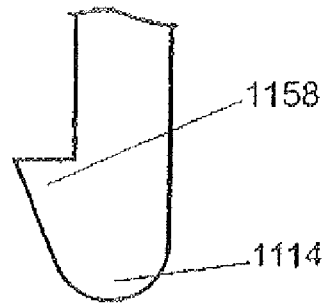
FIG. 6 is a cutaway view of the periphery of the mask body portion.

In the preferred embodiment shown in FIGS. 4 to 6 the bottom 1115 of the inner cushion 1110 fits into a generally triangular cavity 1154 in the hollow body 1102. The cavity 1154 is formed from a flange 1156 running mid-way around the interior of the hollow body.

The outer sheath 1112 fits in place over the top 1117 of the cushion 1110, holding it in place. The sheath 1112 is secured by a snap-fit to the periphery 1114 of the hollow body. In FIGS. 5 to 6 the periphery 1114 is shown including an outer bead 1115. The sheath 1112 includes a matching bead 1159, whereby once stretched around the periphery; the two beads engage to hold the sheath in place.

Figure 10:
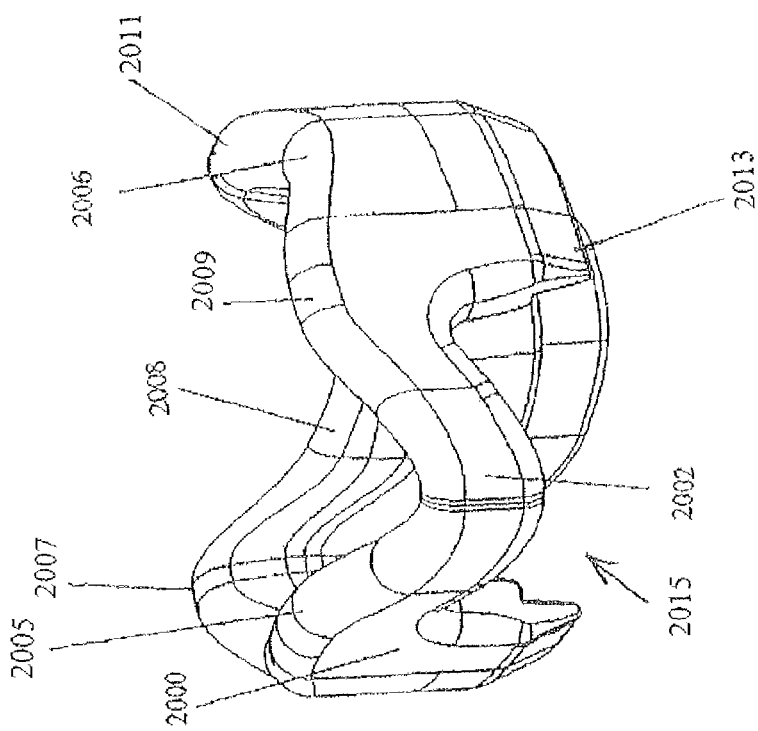
FIG. 10 shows perspective view of a inner sealing (foam) member of the second preferred embodiment of the sealing interface.
Figure 9:
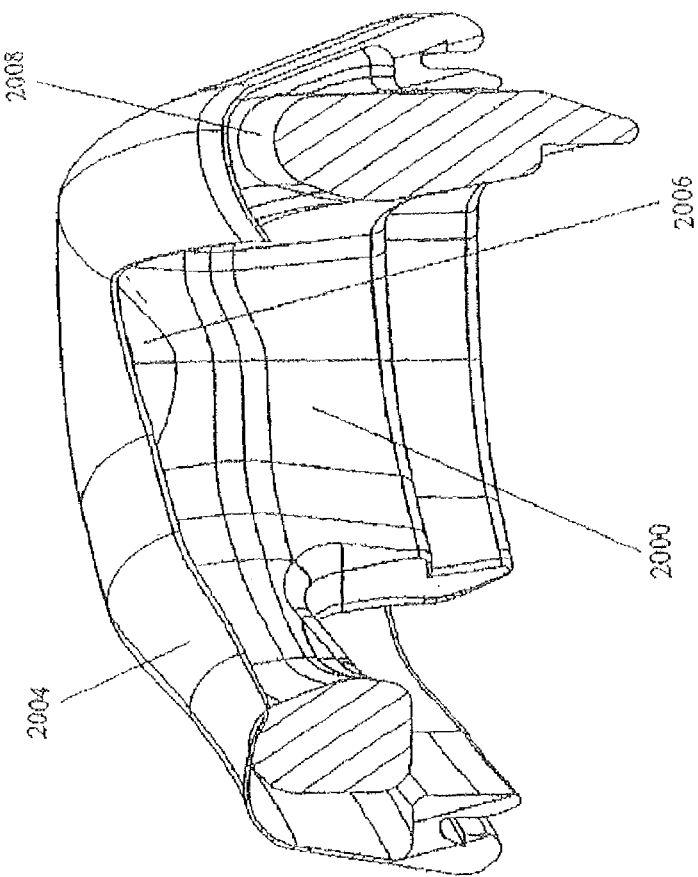
FIG. 9 shows a cross section of a second preferred embodiment of the sealing interface.

A second preferred embodiment to the mask cushion is depicted in FIGS. 9 and 10. In the second embodiment the inner foam cushion 2000 includes a raised bridge 2002 in the nasal bridge region. The raised bridge 2002 can also be described as a cut out section 2015 made in the cushion along the cushion's bottom edge 2013. Also, the notch in the contacting portion (between the inner foam cushion and outer sheath) is less pronounced than proceeding embodiments. However, as the raised bridge 2002 is unsupported due to the cut out section 2015 under the bridge 2013 it is much more flexible and results in less pressure on the nasal bridge of the user. The outer sheath 2004 contacts the foam cushion 2000 throughout the raised bridge 2002. The peaks 2005, 2007, 2009, 2011 in the foam cushion 2000 between each of the indented sections 2006, 2008 and the raised bridge 2002 contact the outer sheath 2004 and when in use the sheath 2004 contacts the facial contours of the user in the regions of these peaks.

Referring particularly to FIG. 10 the foam cushion 2000 includes a cheek contour 2006 to follow the cartilage extending from the middle of the nose, and a contoured lip sealing portion 2008 to seal between the base of the nose and the upper lip.

Figure 11:
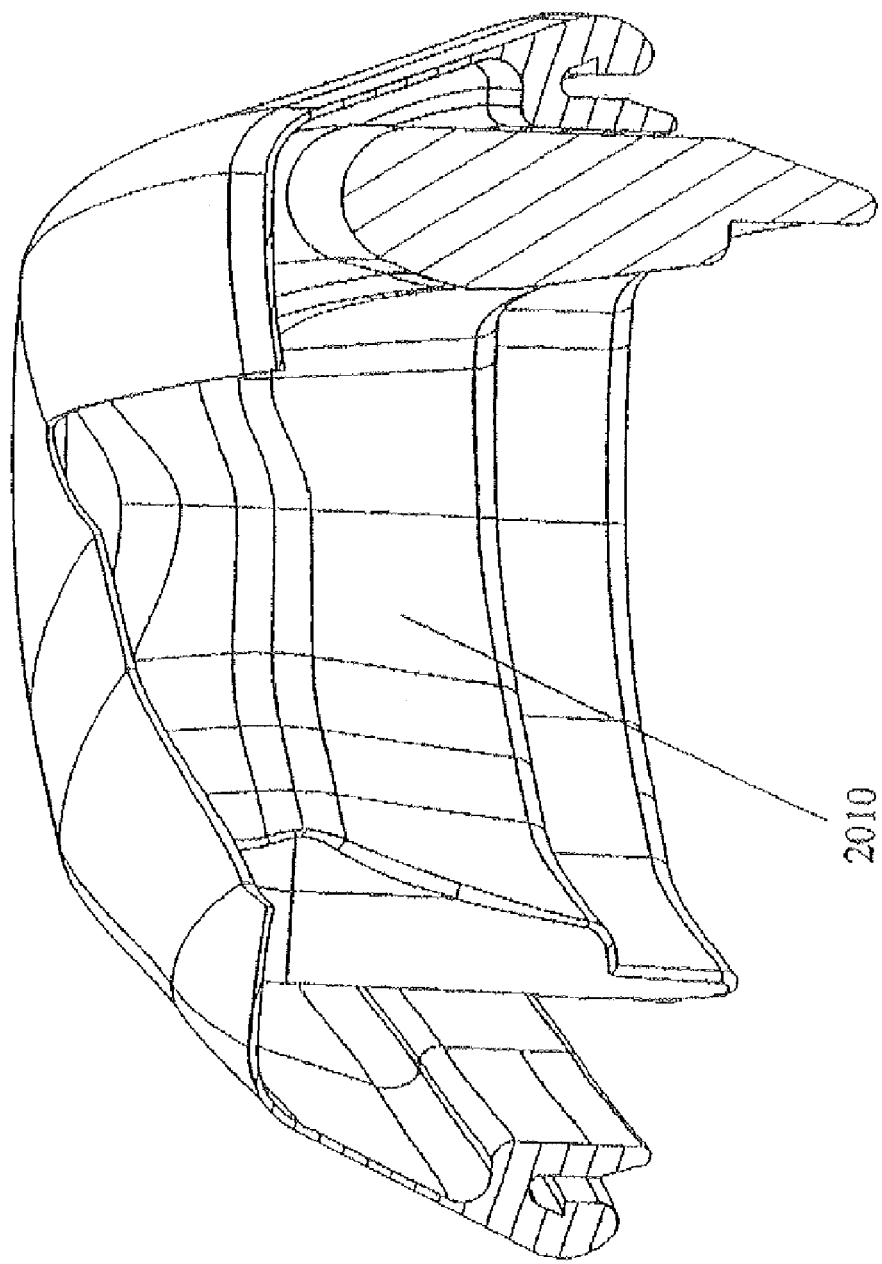
FIG. 11 shows a cross section of a third preferred embodiment of the inner and outer sealing members of the present invention.
Figure 12B:
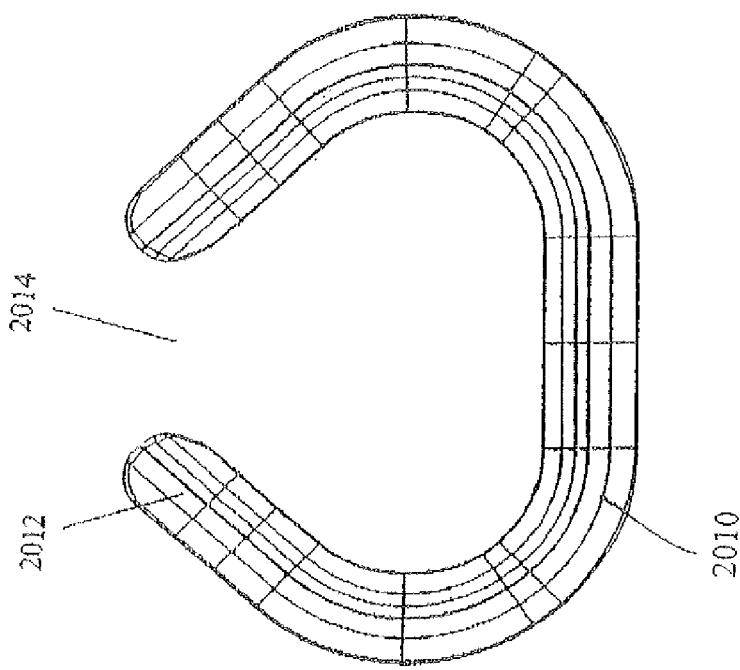
FIG. 12B shows a plan view of the inner sealing (foam) member of the third preferred embodiment of the mask cushion.
Figure 12A:
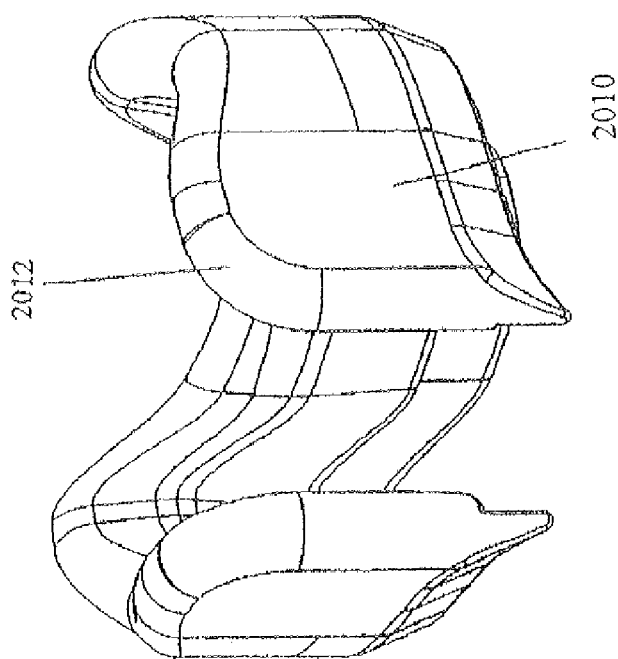
FIG. 12A shows a perspective view of the inner sealing (foam) member of the third preferred embodiment of the sealing interface.

Referring now to FIGS. 11 and 12 a third preferred embodiment of the mask cushion is depicted, in this case, the foam cushion 2010 tapers down 2012 towards the nasal bridge region 2014. For a short portion either side of the nasal bridge region 2014 the foam cushion 2010 is absent, forming a semi annular form in plan view as seen in FIG. 12B.

Figure 18:
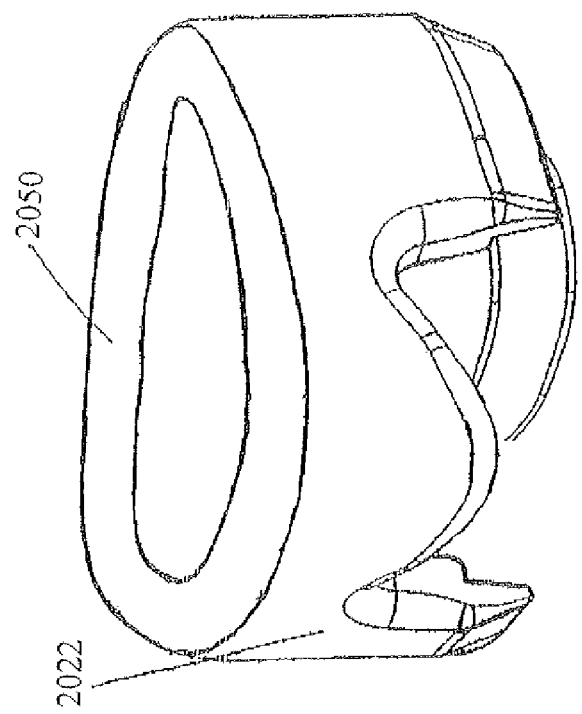
FIG. 18 shows a perspective view of the inner sealing (foam) member according to a ninth preferred embodiment of the sealing interface of the present invention.
Figure 20:
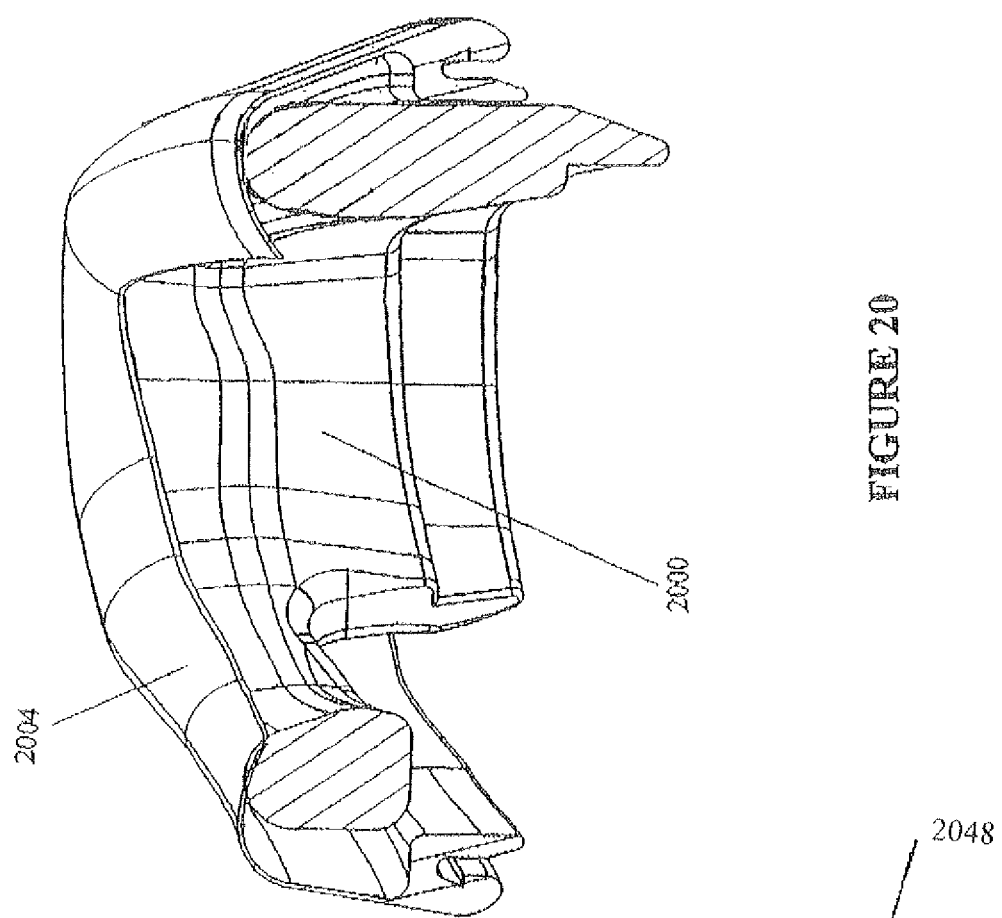
FIG. 20 shows a cross section of a further embodiment of the sealing interface of the present invention where the inner sealing foam member touches the outer sealing member at all times.

Referring to FIG. 13, a fourth preferred embodiment of the mask cushion is depicted. The outer sheath 2020 is adapted to contact the foam cushion 2022 all around, including in the nasal bridge region 2024, and the check contour 2026. FIG. 18 shows the inner foam cushion 2022 where the upper edge 2050 of the cushion does not have any contours and thus will contact the outer sheath all around the edge of the foam cushion. FIG. 20 shows a sealing interface similar to that of FIG. 13 where the inner foam cushion also follows and touches the outer sheath all around its edge.

FIG. 14 illustrates a fifth preferred embodiment of the foam cushion 2030. In the nasal bridge region 2032 the foam cushion includes a lower bridge 2034 and upper bridge 2036. Due to the gap the upper bridge is unsupported to reduce pressure on the user's nasal bridge, but the lower edge 2035 of the foam cushion 2030 is continuous, which aids installation.

Figure 15:
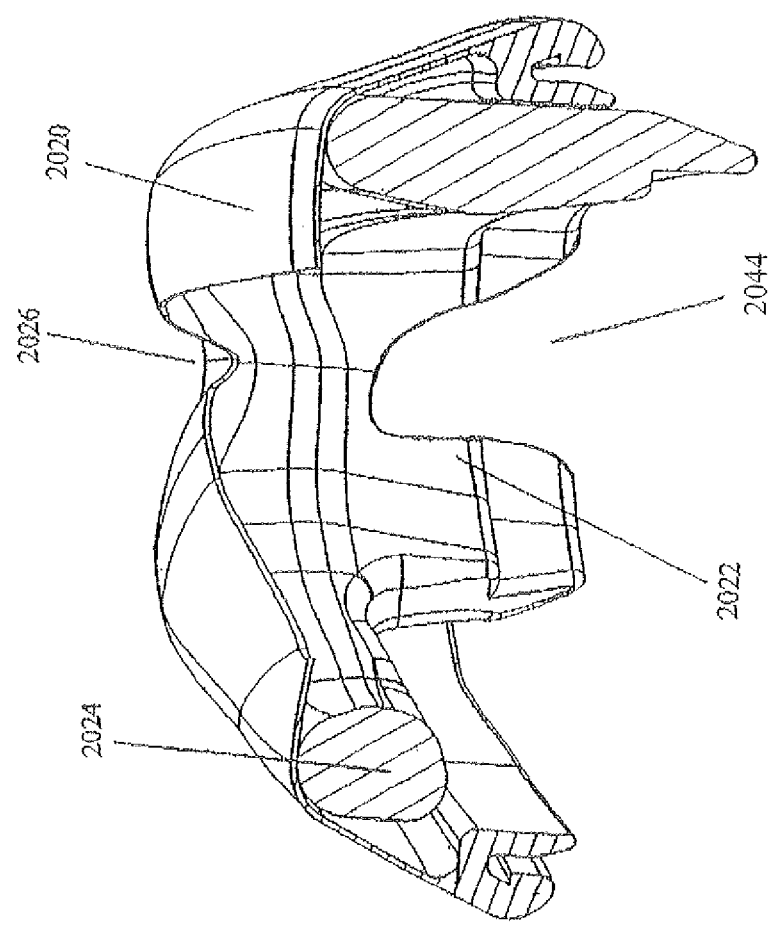
FIG. 15 shows a cross section of a sixth preferred embodiment of the sealing interface of the present invention.
Figure 16:
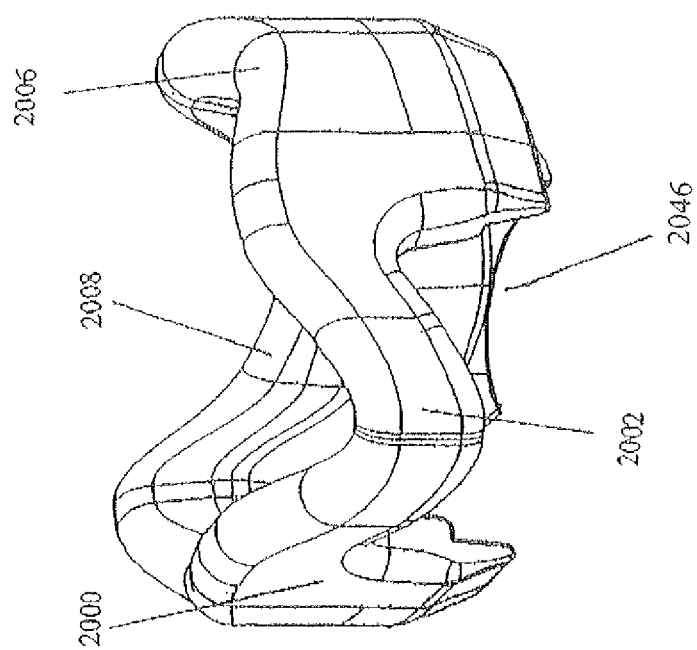
FIG. 16 shows a perspective view of the inner seating (foam) member according to a seventh preferred embodiment of the sealing interface of the present invention.
Figure 17:
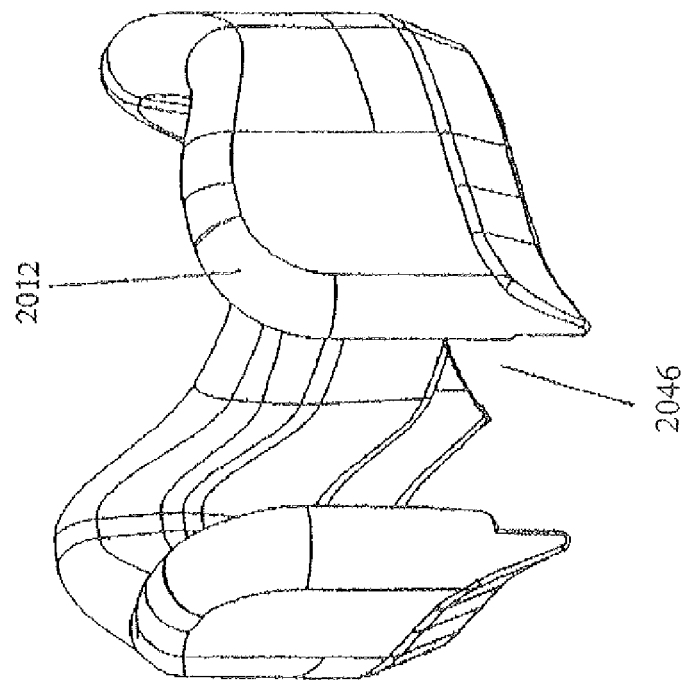
FIG. 17 shows a perspective view of the inner sealing (foam) member according, to an eighth preferred embodiment of the sealing interface of the present invention.

In yet other forms of the sealing interface of the present invention the inner foam cushion may be provided with other contours on the front side of the foam cushion or cut outs on the back side of the foam cushion, so that in the areas where there are regions cut out of the back side of the cushion the cushion is more flexible. In particular, cut outs in the nasal bridge, check and upper lip regions provide the user with a mask cushion that is more flexible and thus more comfortable. FIG. 15 shows an embodiment of an inner foam cushion 2024 that has a curved cut out or dead space 2044 in the cheek region. FIGS. 16 and 17 show embodiments of an inner foam cushion 2000 that has a cut out or dead space 2046 in the area where the user's upper lip rests in the foam. These cut out regions in the cheek or upper lip regions are preferably on the side of the inner cushion that attaches to the nasal mask or hollow body 102, 1102.

Figure 19:
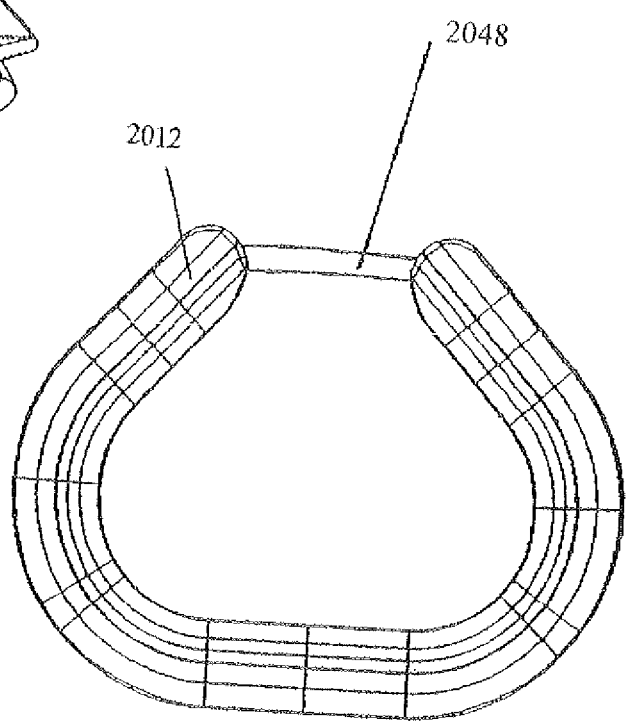
FIG. 19 shows a perspective view of the inner sealing (foam) member according to a tenth preferred embodiment of the sealing interface of the present invention.

A final form of a sealing interface is shown in FIG. 19, here the inner foam member has an annular shape but has a thin bridge or membrane 2048 that extends across and provides flexibility to the nasal bridge region.

Forehead Rest

Figure 7:
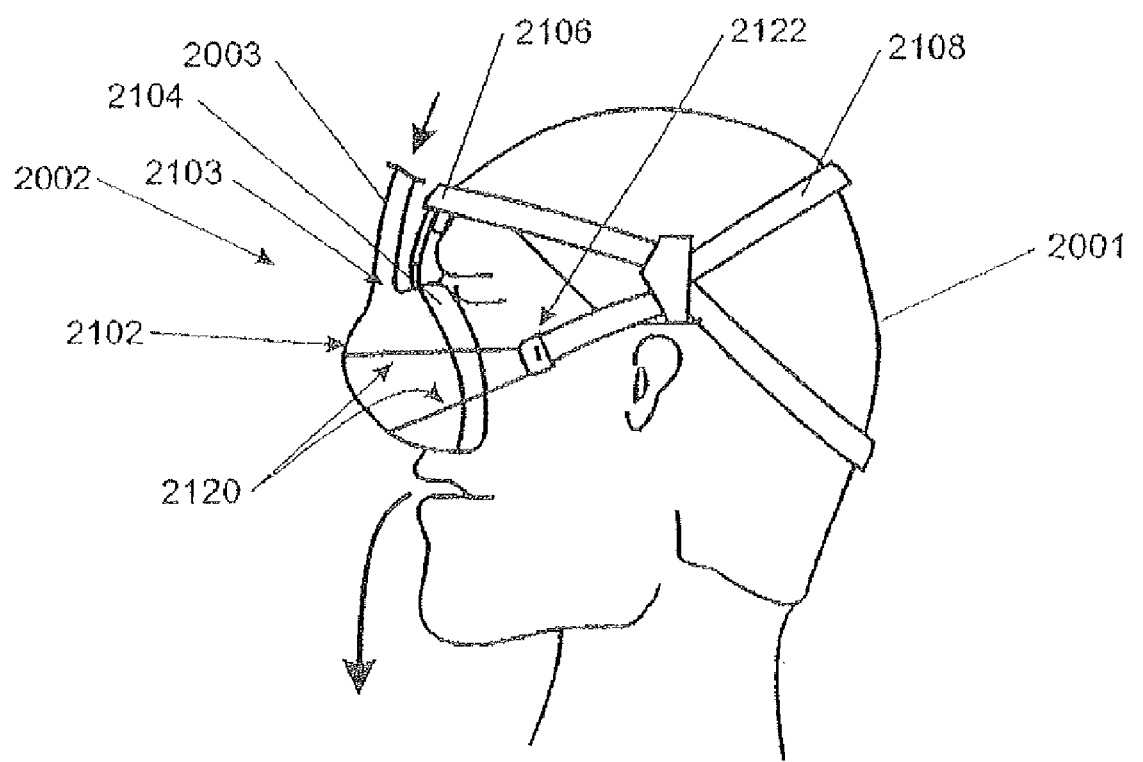
FIG. 7 shows a mask and sealing interface as used with a forehead rest on a user.
Figure 8:
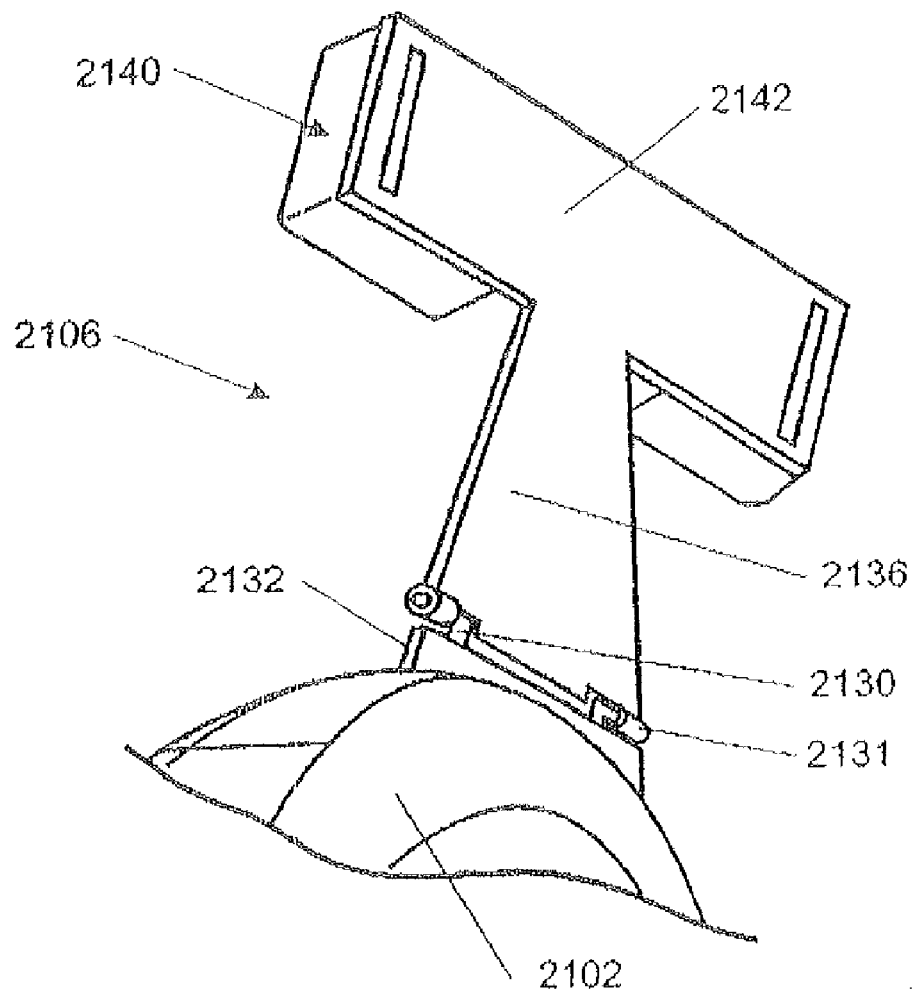
FIG. 8 shows one form of a forehead rest that may be used with the mask and sealing interface of the present invention.

In the preferred embodiment of the present invention the nasal mask 2102 includes a hinged forehead rest 2106 (seen in FIGS. 7 and 8). The attachment of the forehead test 2106 to the hollow body 2102 effectively allows the forehead rest 2106 to move freely in proximity to the user but with no lateral movement.

In one form shown in FIG. 8, pins 2130 are provided mounted on a base 2132 attached to the hollow body 2102. These pins 2130 are co-axial within cylinders 2131 mounted on a bridge member 2136.

At the top end 2142 (around the user's forehead) of the bridge member 2136 harnessing slots 2138 are provided which allow straps from the headgear to be inserted to secure the mask to the headgear. For the users comfort one or more resilient cushions 2140 are provided underneath the top end 2142 of the bridge member 2136, which rest on the forehead of the user. The cushion 2140 might be constructed of silicon or any foam materials as is known in the art for providing cushioning.

For example the forehead rest 2106 described previously may include a weakened section 2130 at its base 2132 which allows the joining member 2136 to pivot from the hollow body 2102. The bridge member extends up to the forehead of the user. In a further alternative the mask may include a vertical upwardly extending inlet. In this case the member 2136 is limited at its base 2132 to either side of the inlet passage. Again the member would then extend to the forehead. Alternatively any well-known form of hinge can be used to provide the pivoting action.

In yet other forms of the present invention the nasal mask may be provided with a fixed forehead rest similar in shape to that shown in FIGS. 7 and 8 but fixed so that the rest is not adjustable. The cut out in the nasal bridge region provides enough flexibility or the mask cushion to provide fitting to a number of different patients, such that the forehead rest does not need to be adjustable or flexible.

We claim:

1. A sealing interface for use with delivery of respiratory gases to a user comprising:
   an inner cushion and an outer sealing member, each having nasal bridge, cheek and upper lip regions that are in use aligned to the nasal bridge, cheek and upper lip regions when in use on the face of said user, said inner cushion and said outer sealing member being separable from one another,
   said inner cushion having a cut out in the nasal bridge region, said inner cushion and said outer sealing member adapted to seal around the facial contours of said user providing a substantially sealed fluid communication to the respiratory tract of said user.

2. A sealing interface according to claim 1 wherein in use said sealing interface is attached to a body that receives said gases, said inner cushion having a first bridging section and said cut out provides a gap between said body and said inner cushion such that said first bridging section can flex within said gap.

3. A sealing interface according to claim 1 wherein in use said sealing interface is attached to a body that receives said gases and said cut out is in said inner cushion on the side of said cushion abutting said body.

4. A sealing interface according to claim 1 wherein in use said sealing interface is attached to a body that receives said gases and said cut out is in said inner cushion on the side of said inner cushion distal said body.

5. A sealing interface according to claim 1 wherein said inner cushion has a cut out region in said cheek region.

6. A sealing interface according to claim 5 wherein said cut out in said cheek region is on the side of said inner cushion that abuts said outer sealing member in use.

7. A sealing interface according to claim 1 wherein said inner cushion has a cut out region in said upper lip region.

8. A sealing interface according to claim 7 wherein said cut out in said upper lip region is on the side of said inner cushion that abuts said outer sealing member in use.

9. A sealing interface according to claim 2 wherein said inner cushion includes a second bridging section, said cut out region disposed between said first bridging section and said second bridging section.

10. A sealing interface according to claim 1 wherein said outer sealing membrane holds said inner cushion in place in use.

* * * * *